US00PP33306P2

(12) United States Plant Patent
Bradford et al.

(10) Patent No.: US PP33,306 P2
(45) Date of Patent: Aug. 3, 2021

(54) CHERRY TREE NAMED 'JONRED IV'

(50) Latin Name: *Prunus avium*
Varietal Denomination: Jonred IV

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 16/974,336

(22) Filed: Jan. 4, 2021

(51) Int. Cl.
*A01H 5/08* (2018.01)
*A01H 6/74* (2018.01)

(52) U.S. Cl.
USPC ..... Plt./181

(58) Field of Classification Search
USPC ..... Plt./156, 181
See application file for complete search history.

(56) References Cited

U.S. PATENT DOCUMENTS

PP12,859 P2 8/2002 Bradford

*Primary Examiner* — Susan McCormick Ewoldt
*Assistant Examiner* — Karen M Redden

(57) ABSTRACT

The present invention relates to a cherry tree, *Prunus avium*, and more particularly to a new and distinct variety broadly characterized by a medium size, moderately vigorous, hardy, self-unfruitful, and productive tree. The fruit matures under the ecological conditions described in early May, with first picking on May 1, 2020. The fruit is medium to large in size, very sweet in flavor, oblate in shape, freestone in type, very firm in texture, pink to moderate red in flesh color, blackish red in skin color, and has a medium length stem that is strongly attached to the fruit.

1 Drawing Sheet

Botanical classification: *Prunus avium.*
Varietal denomination: 'JONRED IV'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of cherry tree, which has been denominated varietally as 'Jonred IV'.

During a typical blooming season we isolate as seed parents individual cherry trees by covering them with screen houses. A hive of bees is placed inside each such house, and bouquets to provide pollen from different cherry trees are placed in buckets near the trees approximately every two days for the duration of the bloom. During 2008 one such house containing 'Glenred' (U.S. Plant Pat. No. 12,859) cherry tree was crossed by us in this manner. To pollinate this cherry, we selected bouquets from several sources of cherry trees without keeping specific written details. Upon reaching maturity the fruit from this cherry tree was harvested and the seeds were removed, cracked, stratified and germinated as a group with the label 'Glenred House'. They were grown as seedlings on their own root in our greenhouse, and upon reaching dormancy transplanted to a cultivated area of our experimental orchard located near Le Grand, Calif. in Merced County (San Joaquin Valley). During the Summer of 2013 the claimed variety was selected by us as a single tree from the group of seedlings described above. Subsequent to origination of the present variety of cherry tree, we asexually reproduced it by budding and grafting in the experimental orchard described above, and such reproductions were true to the original tree in all respects. The reproduction of the variety included the use of 'Colt' (unpatented) rootstock, upon which the present variety was compatible and true to type.

The present variety is most similar to its seed parent, 'Glenred' (U.S. Plant Pat. No. 12,859) cherry, by having a heavy and early bloom, by being self-unfruitful, by having elongated oval leaf glands, by being productive, and by producing medium to large cherries that have a moderately long stem, that are oblate in shape, pink to red in flesh color, and fairly crack resistant, but is distinguished therefrom by blooming about three days earlier and by producing cherries that ripen about nine days earlier, that are a blackish red instead of dark red in skin color at harvest time, that are firmer in texture, that are sweeter in flavor, that are semi-freestone instead of clingstone in type, and that have a much stronger stem attachment.

SUMMARY OF VARIETY

In summary, the present cherry variety is characterized by a medium size, moderately vigorous, hardy, self-unfruitful, and productive tree. The fruit matures under the ecological conditions described in early May, with first picking on May 1, 2020. The fruit is medium to large in size, very sweet in flavor, oblate in shape, freestone in type, very firm in texture, pink to moderate red in flesh color, blackish red in skin color, and has a medium length stem that is strongly attached to the fruit.

DRAWING

The accompanying photograph displays four whole fruits with the stems attached, two whole fruits detached from the stems to exhibit the skin color and form, a sectioned fruit to reveal the flesh, fibers, and stone, two insets depicting flowers and buds, a typical tip shoot, and several leaves, all typical of the subject variety.

POMOLOGICAL CHARACTERISTICS

Referring now more specifically to the pomological characteristics of this new and distinct variety of cherry tree, the following has been observed under the ecological conditions prevailing near Le Grand, Merced County (San Joaquin Valley), Calif., and was developed at the state of firm ripe on May 7, 2020, on the original tree during its twelfth growing season. All major color code designations are by reference to the Inter-Society Color Council, National Bureau of Standards. Common color names are also used occasionally.

PARENTAGE

Seed parent: 'Glenred' cherry (U.S. Plant Pat. No. 12,859).
Pollen parent: Unknown.

TREE

Size: Medium, maintained to a height of 8' [2.44 m.] and a spread of 9' [2.74 m.] after twelve growing seasons utilizing typical pruning.

Vigor: Moderately vigorous, responding typically to irrigation and fertilization. The plant should be grown on a standard commercial rootstock for production purposes.

Growth: Spreading and open.

Form: Central leader.

Hardiness: Half hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive.

Fertility: Self-unfruitful, must be cross pollinated by another early blooming cherry variety, such as 'Red Glen' (U.S. Plant Pat. No. 12,859).

Bearing: Regular, dependent upon seasonal blooming weather.

Leaf bud burst: Toward the end of flowering.

Trunk:

- *Size.*—Medium, reaching a maximum diameter of 4¾" [120.7 mm.] after the twelfth growing season.
- *Texture.*—Medium to shaggy.
- *Bark color.*—A Light grayish brown [60. l.gy.Br] and Light brownish gray [63. l.brGy] variegation with Brownish gray [64. brGy] crevices present.
- *Lenticels.*—Approximate Number Per Square Inch: 8. Color: Strong yellowish brown [74. s.yBr]. Average Size: Length is 7/16" [11.1 mm.] with a width of 1/16" [1.6 mm.]. Shape: Elongated.

Branches:

- *Size.*—Medium to slender, diameter of main scaffold measured 12" above the first hanger is 3½" [88.9 mm.], and the first hanger diameter is 1¼" [31.8 mm.].
- *Texture.*—Smooth on first and second year wood, increasing roughness with age.
- *Color.*—1st Year Wood topside: Grayish red [19. gy.R]. 1st Year Wood underside: Brilliant yellow green [116. brill.YG]. 2nd Year Wood: A Grayish brown [61. gy.Br] and Moderate brown [58. m.Br] variegation with Dark grayish brown [62. d.gy.Br] crevices present.
- *Lenticels.*—Number Per Square Inch: About 22 on second year wood. Color: Strong yellowish brown [74. s.yBr]. Average Size: Medium, length is 1/8" [3.2 mm.] and width is 1/32" [0.8 mm.]. Shape: Elongated.

Leaves:

- *Size.*—Medium to large. Average Length: 4⅞" [123.8 mm.]. Average Width: 2⅛" [53.9 mm.].
- *Arrangement.*—Alternate.
- *Thickness.*—Medium.
- *Form.*—Elliptical.
- *Apex.*—Acuminate.
- *Base.*—Acute.
- *Surface.*—Smooth on both sides.
- *Color.*—Dorsal Surface: Moderate olive green [125. m.OlG]. Ventral Surface: Moderate yellow green [120. m.YG].
- *Red midvein.*—Absent.
- *Margin.*—Finely serrate to serrate.
- *Venation.*—Pinnately net veined.
- *Vein color.*—Brilliant yellow green [116. brill.YG].
- *Petiole.*—Average Length: 1 13/16" [46.0 mm.]. Average Thickness: 1/16" [1.6 mm.].
- *Color.*—Dark purplish red [259. d.pR] on the topside, Brilliant yellow green [116. brill.YG] underneath.
- *Stipules.*—Number: 2 per leaf, up to 6 per growing tip. Average Length: ½" [12.7 mm.]. Color: Brilliant yellow green [116. brill.YG] turning Moderate olive brown [95. m.OlBr] with age.
- *Glands.*—Number: Usually 2 per leaf. Position: Located in pairs, slightly alternate. Size: Large, 1/16" [1.6 mm.] in length. Form: Oval, elongated. Color: Brilliant greenish yellow [98. brill.gY] with a Moderate reddish orange [37. m.rO] center.
- *Leaf buds.*—Pointed.

Flower buds:

- *Hardiness.*—Hardy with respect to central California blooming season.
- *Diameter.*—Typically 5/16" [7.9 mm.] 3 days before bloom.
- *Length.*—Typically ⅝" [15.9 mm.] 3 days before bloom.
- *Form.*—Not appressed.
- *Surface.*—Very slightly pubescent.
- *Tip color.*—White [263. White].

Flowers: Perfect, complete, perigynous, usually a single pistil, typically about twenty stamens, five sepals and petal locations alternately positioned.

- *Average flower diameter.*—1¾" [44.5 mm.].
- *Average flower depth.*—½" [12.7 mm.] when fully open.
- *Average pedicel length.*—7/16" [11.1 mm.].
- *Number of petals.*—Usually five, a few extra petal fragments typically observed.
- *Petal arrangement.*—Overlapping.
- *Petal shape.*—Circular to slightly obovate.
- *Petal margin.*—Somewhat wavy with an occasional notch.
- *Average petal diameter.*—11/16" [17.5 mm.].
- *Average petal length.*—¾" [19.1 mm.].
- *Petal apex.*—Rounded.
- *Petal base.*—Obtuse.

*Petal color.*—White [263. White] on both sides.
*Anther color.*—Moderate orange yellow [71. m.OY].
*Stigma color.*—Vivid greenish yellow [97. v.gY].
*Stigma position.*—Typically located about even with the nearby anthers.
*Stamen position.*—Typically located about 1/32" [0.8 mm.] below the petals.
*Ovary.*—Non-pubescent.
*Sepal color.*—Grayish purplish red [262. gy.pR] over Moderate yellow green [120. m.YG] on the outer surface. The inner surface is Light yellow green [119. l.YG].
*Sepal outer surface.*—Slightly pubescent.
*Sepal length.*—3/8" [9.5 mm.].
*Sepal width.*—3/16" [4.8 mm.].
*Sepal apex.*—Elliptical to match the sepal length and width.
*Sepal margin.*—Fairly smooth.
*Average pistil length.*—11/16" [17.5 mm.].
*Average stamen length.*—9/16" [14.3 mm.].
*Fragrance.*—Moderate.
*Pollen production.*—Moderate.
*Pollen color.*—Strong yellow [84. s.Y].
*Bloom density.*—Heavy.
*Blooming period.*—Early, blooms three days earlier than 'Glenred' (U.S. Plant Pat. No. 12,859) cherry.
*Onset of bloom.*—One percent on Mar. 5, 2020.
*Date of full bloom.*—Mar. 12, 2020.
*Duration of bloom.*—One to two weeks, dependent on ambient temperature.
*Number per cluster.*—Usually 2 to 6, 3 average.

FRUIT

Maturity when described: Firm ripe, May 7, 2020.
Date of first picking: May 1, 2020.
Date of last picking: May 12, 2020.
Size: Uniform, medium to large.
*Average diameter axially.*—1" [25.4 mm.].
*Average diameter across cheek plane.*—1 3/16" [30.2 mm.].
*Average diameter across suture plane.*—1" [25.4 mm.].
*Typical weight.*—0.43 ounces [12.2 grams].
Form: Uniform, symmetrical, oblate to round ovate.
*Axial view form.*—Elliptical.
*Suture plane form.*—Oval.
*Cheek plane form.*—Oblate.
Suture: A Dark red [16. d.R] line located in a very shallow trough extending from the base past the pistil point.
Ventral surface: Rounded, lipped on both sides.
Lips: Equal.
Cavity: Flaring, rounded, suture showing on one side.
*Depth.*—1/8" [3.2 mm.].
*Breadth.*—7/16" [11.1 mm.].
Base: Truncate, slightly cordate if viewed parallel to the suture.
Apex: Rounded.
Pistil point: A Light yellow [86. l.Y] dot depressed within the suture.
Stem: Medium to long.
*Average length.*—1 1/2" [38.1 mm.].
*Average width.*—1/16" [1.6 mm.].
*Attachment.*—Strong.
Skin:
*Thickness.*—Medium.
*Surface.*—Smooth.
*Tenacity.*—Tenacious to the flesh.
*Astringency.*—Moderate.
*Tendency to crack.*—None observed.
*Color.*—Blackish red [21. blackish R] smoothly blending to a Very dark red [17. v.d.R] background.
Flesh:
*Color.*—Vivid deep red [14. v.deep R] near the skin and stone, Moderate pink [5. m.Pk] toward the middle, and Light pink [4. l.Pk] fibers throughout.
*Surface of pit cavity.*—Covered with Dark red [16. d.R] fibers.
*Amygdalin.*—Moderate.
*Juice.*—Abundant, rich.
*Juice color.*—Deep red [13. deep R].
*Texture.*—Firm, crisp.
*Fibers.*—Abundant, fine, tender.
*Ripens.*—Fairly evenly.
*Flavor.*—A very tasty blend of acid and sugar, typically 23 brix.
*Aroma.*—Very slight.
*Eating quality.*—Excellent.

STONE

Type: Fairly freestone.
Form: Oval.
Hilum: Narrow, oblong.
Base: Rounded.
Apex: Acute.
Sides: Fairly equal.
Surface: Fairly smooth.
External color of stone: Dark orange yellow [72. d.OY].
Pit wall color when cracked: Pale orange yellow [73. p.OY].
Cavity surface color: Light yellowish brown [76. l.yBr].
Average pit wall thickness: 1/16" [1.6 mm.].
Average length: 1/2" [12.7 mm.].
Average width: 7/16" [11.1 mm.].
Average breadth: 3/8" [9.5 mm.].
Tendency to split: None observed.
Kernel:
*Form.*—Oval.
*Skin color.*—Pale yellow [89. p.Y] when first removed.
*Pellicle color.*—Light olive brown [94. l.OlBr].
*Taste.*—Bitter.
*Viable.*—Yes.
*Average length.*—5/16" [7.9 mm.].
*Average width.*—1/4" [6.4 mm.].
*Amygdalin.*—Moderate.

USE

Market: Fresh market and long distance shipping.
Keeping quality: Good, fruit quality observed to remain in good condition after 14 days in standard cold room at 36° Fahrenheit [2° Celsius].
Shipping quality: Good.
Resistance to insects: Not tested.
Resistance to diseases: Not tested.

OTHER NOTES

Although the new variety of cherry tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of cherry tree, substantially as illustrated and described, that is most similar to its seed parent, 'Glenred' (U.S. Plant Pat. No. 12,859) cherry, by having a heavy and early bloom, by being self-unfruitful, by having elongated oval leaf glands, by being productive, and by producing medium to large cherries that have a moderately long stem, that are oblate in shape, pink to red in flesh color, and fairly crack resistant, but is distinguished therefrom by blooming about three days earlier and by producing cherries that ripen about nine days earlier, that are a blackish red instead of dark red in skin color at harvest time, that are firmer in texture, that are sweeter in flavor, that are semi-freestone instead of clingstone in type, and that have a much stronger stem attachment.

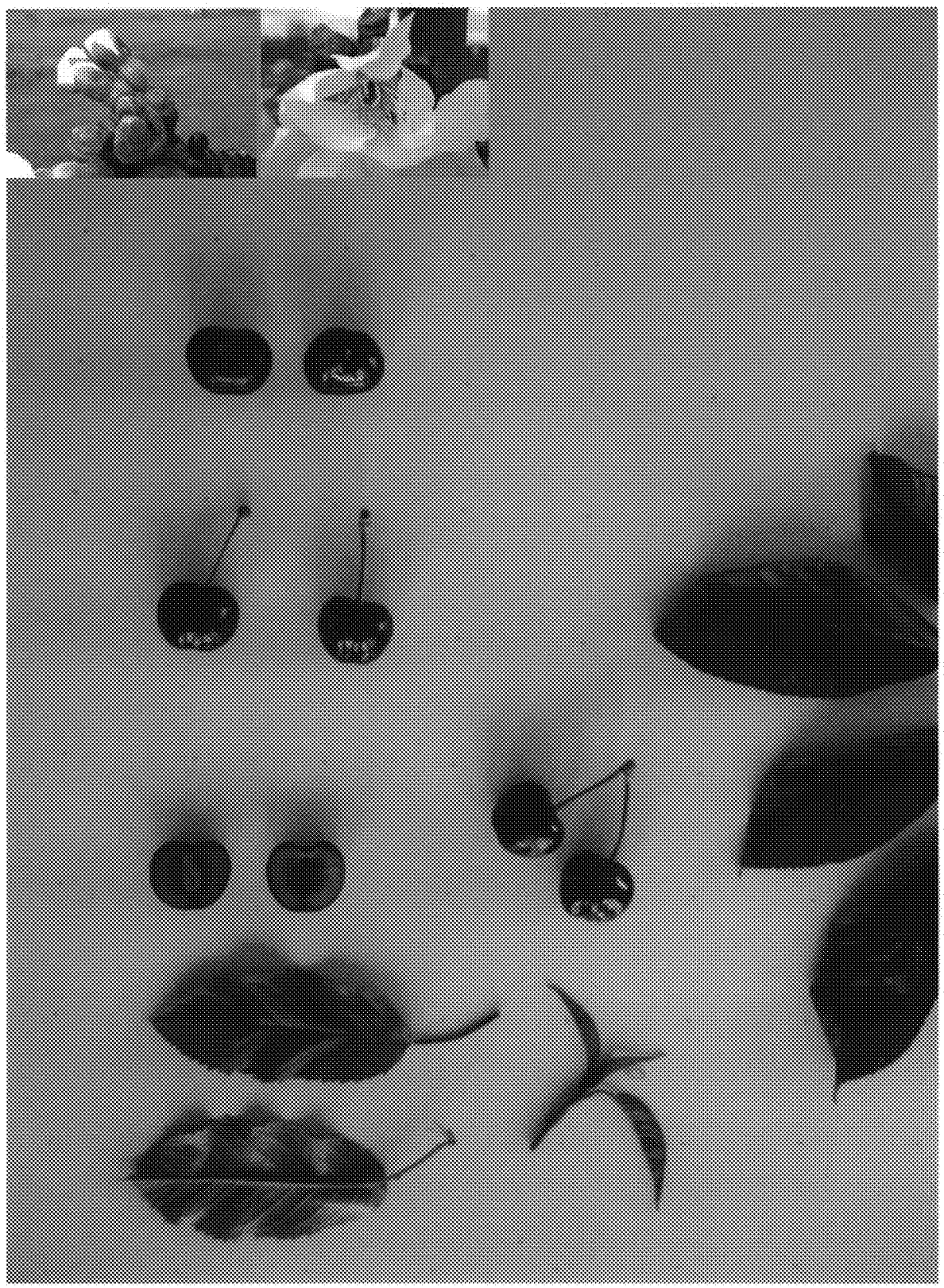

* * * * *